United States Patent [19]

Elsner

[11] 4,155,243
[45] May 22, 1979

[54] CALIBRATION ASSEMBLY FOR NUCLEAR REACTOR VESSEL INSPECTION APPARATUS

[75] Inventor: Hans J. Elsner, Pittsburgh, Pa.

[73] Assignee: Westinghouse Electric Corp., Pittsburgh, Pa.

[21] Appl. No.: 805,545

[22] Filed: Jun. 10, 1977

[51] Int. Cl.² ............................................. G01N 29/04
[52] U.S. Cl. ........................................ 73/1 R; 73/623
[58] Field of Search .................... 73/1 R, 1 DV, 67.7, 73/67.8 R, 67.8 S, 71.5 US; 310/335; 340/5 C, 8 FT

[56] References Cited

U.S. PATENT DOCUMENTS

| | | | |
|---|---|---|---|
| 3,371,524 | 3/1968 | Wloszek | 73/1 R X |
| 3,908,439 | 9/1975 | Pelak et al. | 73/1 R |
| 3,933,026 | 1/1976 | Ham et al. | 73/1 R |
| 3,943,756 | 3/1976 | Aubert et al. | 73/67.8 S |
| 4,008,455 | 2/1977 | Pedersen | 340/1 R |

Primary Examiner—Charles A. Ruehl
Attorney, Agent, or Firm—L. A. DePaul

[57] ABSTRACT

A removable calibration assembly is disclosed which can be utilized to verify the angular mounting of transducers in an array employed in the inspection apparatus, to calibrate one axis of movement of the array with reference to a zero starting point or to measure and calibrate for the speed per unit of distance of the transducer's ultrasonic beam in the actual operating medium. The calibration assembly includes both a relatively infinitely large and a relatively infinitely small reflecting surface separated by known distances and a plurality of truncated cones, the tips of which are machined or adjusted to those angles at which certain of the transducers are to be mounted in the array. In addition, clamping means for securing the calibration assembly to the inspection apparatus at a predetermined orientation is provided.

6 Claims, 4 Drawing Figures

CALIBRATION ASSEMBLY FOR NUCLEAR REACTOR VESSEL INSPECTION APPARATUS

CROSS-REFERENCE TO RELATED APPLICATIONS

This application is hereby cross-referenced to the following patent applications which were filed on Mar. 25, 1977 and which are commonly assigned:

U.S. patent application Ser. No. 781,403 filed Mar. 25, 1977 entitled "Positioning Means For Circumferentially Locating Inspection Apparatus In A Nuclear Reactor Vessel", filed in the name of David C. Burns;

U.S. patent application Ser. No. 781,381 filed Mar. 25, 1977 entitled "Segmented Articulating Manipulator Arm For Nuclear Reactor Vessel Inspection Apparatus", filed in the names of David C. Burns and Lanson Y. Shum;

U.S. patent application Ser. No. 781,401 filed Mar. 25, 1977 entitled "Variable Mounting Assembly For Transducers Employed In Nuclear Reactor Vessel Inspection Apparatus", filed in the names of Hans J. Elsner, Ronald F. Antol and Raymond P. Castner;

U.S. patent application Ser. No. 781,390 filed Mar. 25, 1977 entitled "Pulley System Including Emergency Locking Means For Nuclear Reactor Vessel Inspection Apparatus", filed in the name of Renato D. Reyes;

U.S. patent application Ser. No. 781,401 filed Mar. 25, 1977 entitled "Emergency Braking System For Nuclear Reactor Vessel Inspection Apparatus", filed in the name of Renato D. Reys;

U.S. patent application Ser. No. 781,396 filed Mar. 25, 1977 entitled "Emergency Disconnect Means For The Manipulator Arm Of A Nuclear Reactor Vessel Inspection Apparatus", filed in the names of Arthur F. Jacobs and Duane W. Morris;

U.S. patent application Ser. No. 781,404 filed Mar. 25, 1977 entitled "Pressurized Cabling And Junction Boxes For Nuclear Reactor Vessel Inspection Apparatus", filed in the names of Charles V. Fields and Raymond P. Castner; and U.S. patent application Ser. No. 781,402 filed Mar. 25, 1977 entitled "Emergency Retraction Means For The Manipulator Arm Of A Nuclear Reactor Vessel Inspection Apparatus", filed in the names of Arthur F. Jacobs and Duane W. Morris.

Reference is also made to the commonly filed and assigned U.S. patent application Ser. No. 805,546 filed June 10, 1977 entitled "Positioning Calibration Apparatus For Transducers Employed In Nuclear Reactor Vessel Inspection Apparatus", filed in the name of Hans J. Elsner.

All of the foregoing applications are hereby incorporated herein by reference.

BACKGROUND OF THE INVENTION

Nuclear reactor vessels employed in the commercial generation of electrical power are of two types; the pressurized water type or the boiling water type. In either case, the reactor vessel utilizes a generally cylindrical metallic container having a base and a top flange welded thereto. The main cylinder portion itself usually comprises a series of lesser cylinders welded to each other. In addition, a plurality of circumferentially spaced nozzles extend through the main cylinder wall and are welded thereto. Thus, numerous welds are necessarily used in fabricating the reactor vessel, in mating the top flange to the main cylindrical body and in securing the inlet and outlet nozzles to the reactor vessel wall.

The reactor vessel, in use, is encased in a thick concrete containment area. However, the structural integrity of the reactor vessel, the concrete containment notwithstanding, due to the operating environment is of critical importance.

The weld areas of the reactor vessel are, of course, inspected prior to its initial use. Such inspection is carried out with all portions of the vessel relatively accessible to an inspection device prior to its encasement in the concrete containment. However, in-service inspection of the reactor vessel welds is not only desirable, but is mandated under governmental regulations.

Under such regulations, it is required that the vessel weld areas be subjected to periodic volumetric examination whereby the structural integrity of the vessel is monitored. Due to the nature of an in-service inspection, the device designed to accomplish the specified weld examinations must be capable of successfully operating in an underwater and radioactive environment under remote control while maintaining a high degree of control over the placement and movement of the inspection sensors.

The operating constraints are further complicated by the variety of reactor vessel sizes to which the inspection device must be able to be accommodated. Furthermore, the inspection device must not only be compatible with the weld placements of the reactor vessels now in use, but must also be sufficiently versatile to adapt to inspection duty in future vessels. In addition, the inspection device must be arranged in its use to have only minimal impact with normal refueling and maintenance operations.

The use of ultrasonic transducers to inspect metal welds is known. One such system is described in the periodical *Materials Evaluation,* July 1970, Volume 28, No. 7, at pages 162–167. This article describes a transmitter-receiver type ultrasonic inspection system for use in the in-service inspection of nuclear reactor vessels. The positioning arrangement for the transducers uses a track which is mounted on the interior wall of the reactor vessel.

A method and apparatus for ultrasonic inspection of a pipe from within is disclosed in U.S. Pat. No. 3,584,504. In the apparatus disclosed therein, a transducer array is mounted on a carrier which is rotatable, by means of a central shaft of the apparatus, within the pipe.

In U.S. Pat. No. 3,809,607, a nuclear reactor vessel in-service inspection device is detailed, which device is adapted to permit remotely controlled and accurate positioning of a transducer array within a reactor vessel. This device comprises a positioning and support assembly consisting of a central body portion from which a plurality of radially directed support arms extend. The ends of the support arms are extended to and adapted for being seated on a predetermined portion of the reactor vessel to define a positional frame of reference for the inspection device relative to the reactor vessel itself. Repositioning and support assemblies are provided and include integral adjustment means which cooperate to permit the simultaneous variation of the extension of the support arms thereby allowing the inspection device to fit reactor vessels of differing diameters. A central column is connected to the positioning and support assemblies, which central column extends along the longitudinal axis thereof. One or more movable inspection assemblies are connected to the central column and include drive and position indicating means. Three specific inspection subassemblies include a flange scanner, a nozzle scanner and a vessel scanner. Each of these scanners employ multiprobe transmitter-receiver ultrasonic transducers to permit more accurate volumetric plotting of the integrity of the welds used in fabricating the reactor vessel.

Since the development of the above-identified inspection devices, the original inspection code has been amended to call for more reliable and more rigorous inspections. In addition, these prior art devices were unable to accurately measure or reach certain weld areas of the reactor vessel. Still other drawbacks in the prior art inspection devices were the reliability and speed of the actual inspection effort.

One particular problem which was not solved by any of the above-described prior art devices was that of calibrating or referencing a zero start point for the vertical axis of transducer movement within the reactor vessel so that the exact location of the array and derivatively of any weld defect would be known. Another problem not satisfactorily solved by the prior art devices concerned the integrity of transducer mounting, particularly where the manipulator arm or the transducer array carried thereon bumps into or impacts the vessel. In such an instance, it would otherwise be necessary to withdraw the inspection apparatus to verify that there had been no change in the alignment of any transducer, a procedure which would result in at least a two shift delay due to decontamination procedures along. Yet another problem left unsolved by these prior art devices was that of ascertaining the speed per unit of distance in the operating medium of the transducer beam prior to the actual inspection.

SUMMARY OF THE INVENTION

Accordingly, there is provided a calibration assembly for ultrasonic transducers which includes a relatively infinitely large reflecting surface and a relatively infinitely small reflecting surface separated by known appropriate distances. Also included on the large reflecting surface is a plurality of reflecting surfaces, each at an appropriate angle, for verifying proper mounting of commensurately angled transducers mounted in the transducer array of a nuclear vessel inspection apparatus.

The calibration assembly further includes means for clamping itself, in a predetermined orientation, to a portion of the inspection apparatus. The means for clamping utilizes an appropriately configured keyway designed to lockingly accommodate a mating key on that portion of the inspection apparatus to which the calibration assembly is to be secured. The location of the key and keyway can be reversed.

DESCRIPTION OF THE PREFERRED EMBODIMENT

Figure 1:
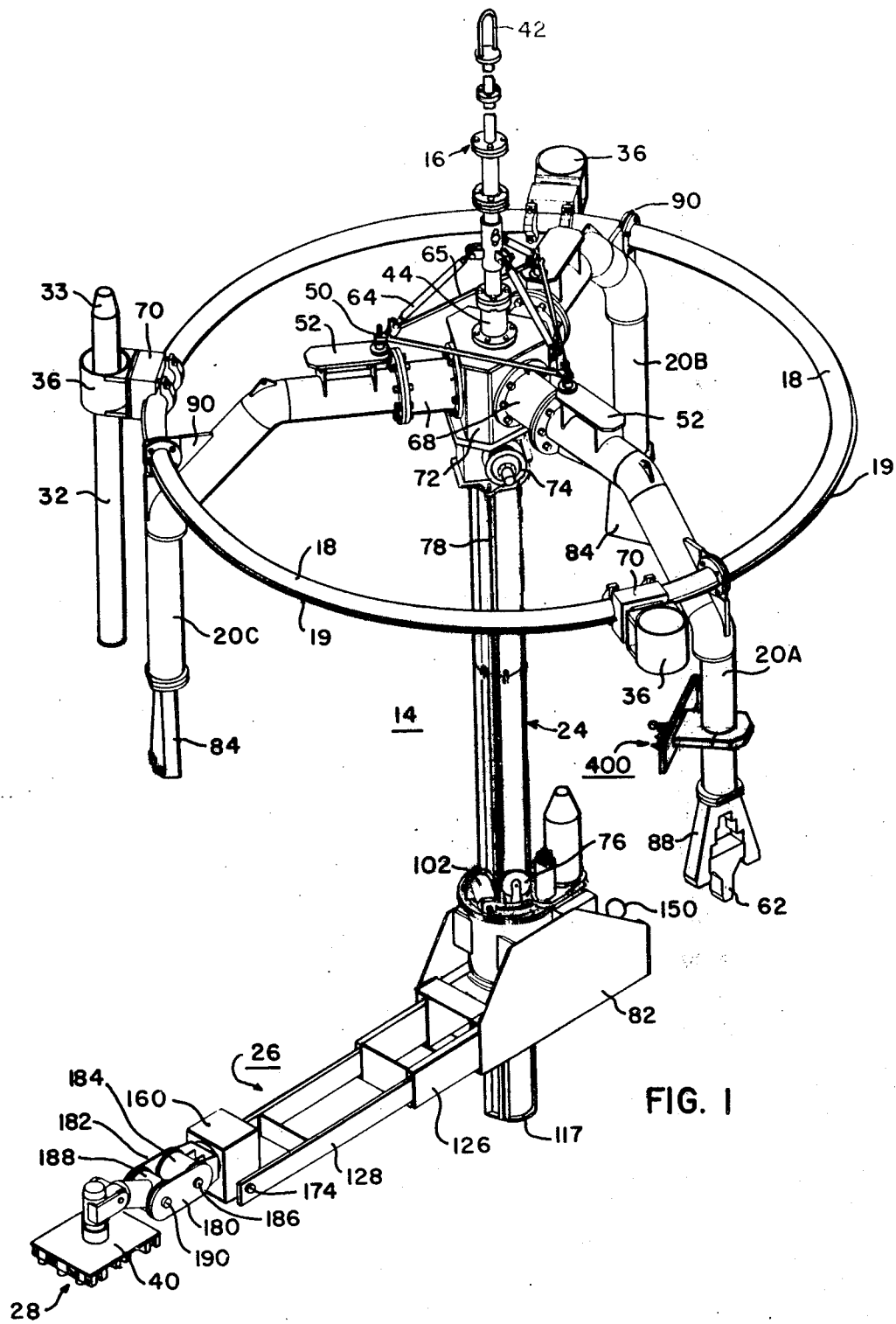
FIG. 1 is an isometric view of nuclear vessel inspection apparatus having the present invention secured to a portion thereof.

Referring now to the drawings wherein identical reference numerals have been used in the several views to identify like elements, FIG. 1 illustrates an isometric view of a nuclear reactor vessel inspection apparatus 14. The inspection apparatus 14 is more fully described in the above cross-referenced applications and need not, therefore, be similarly described herein. Additional and specific details thereof may be had by reference to any one of the cross-referenced applications, for example, U.S. patent application Ser. No. 781,380 filed Mar. 25, 1977.

For purposes of the present invention, it is sufficient to note that the inspection apparatus 14 is lowered into and seated within a reactor vessel. The vessel inspection is then carried out by driving a manipulator arm 26, which carries a transducer array 28, along or about nine axes of movement to effect interrogation of the vessel weld integrity.

Figure 2:
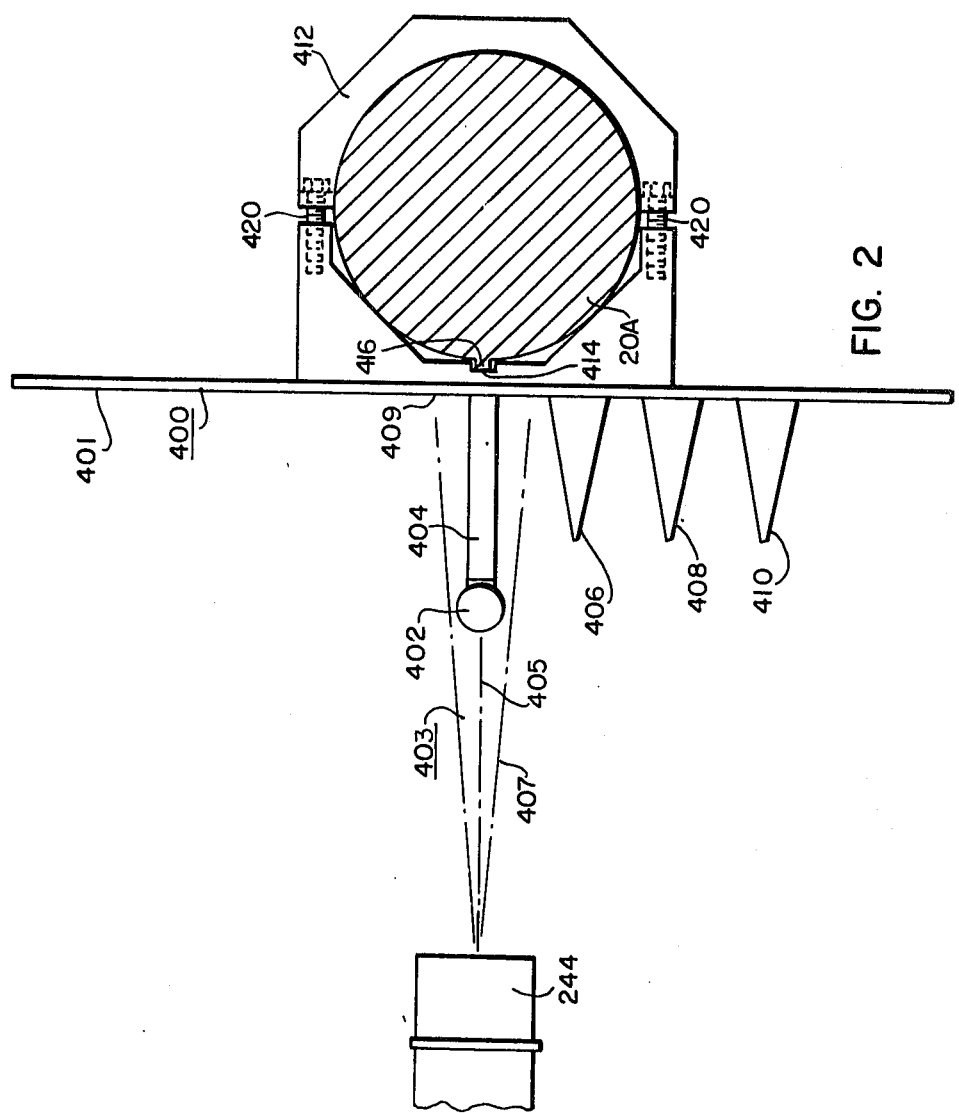
FIG. 2 is a schematic side view, partly in section, of a calibration assembly shown in FIG. 1, as it would be targeted by a transducer in use.
Figure 4:
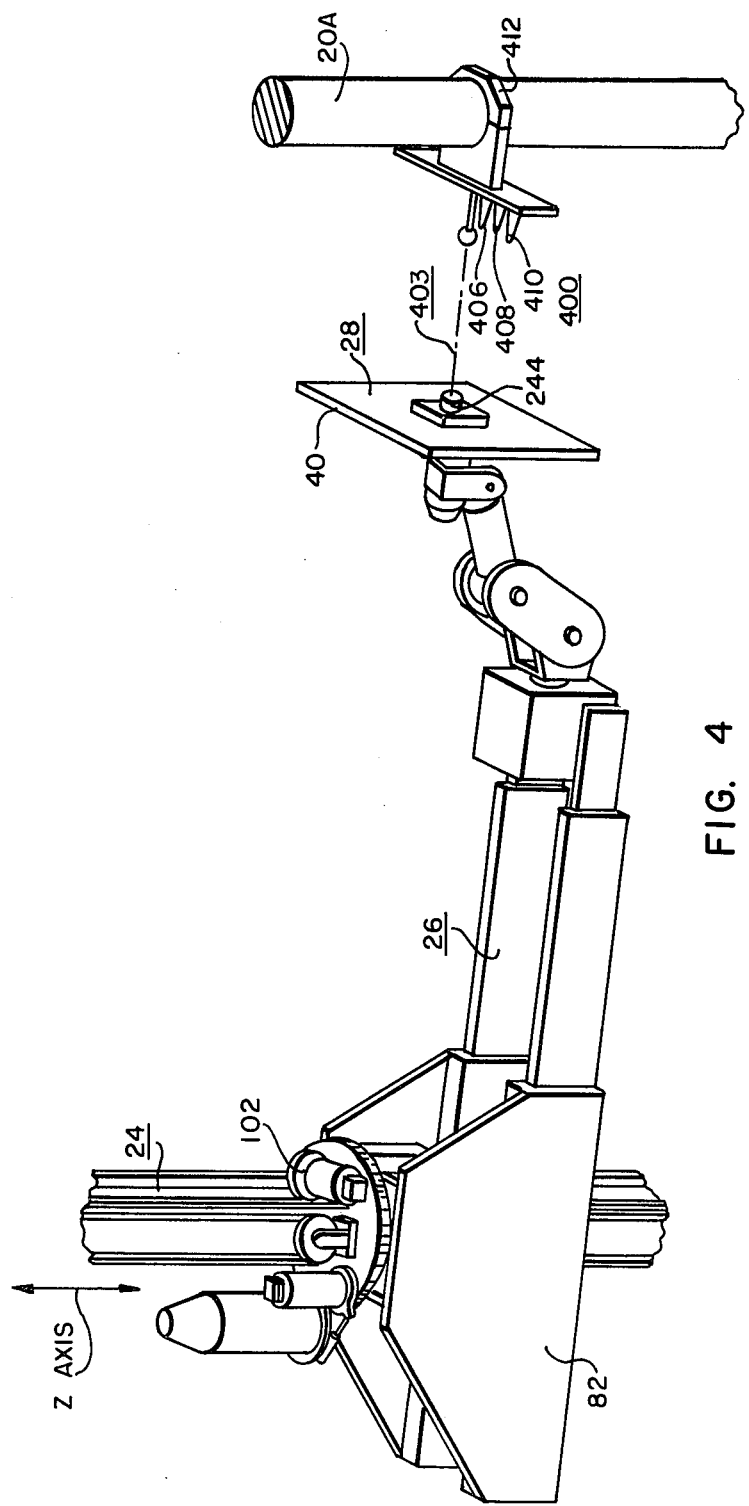
FIG. 4 is an isometric schematic illustration of the manipulator arm and transducer array of the inspection apparatus in use with the calibration assembly of the present invention.

As previously noted, it is required in order to insure test authenticity, that the starting point of the transducer array, be accurately known since the location of the vessel welds or discovered defects is derivable directly therefrom. Accordingly, at the start of each test and during specified intervals therein, the transducer array 28 is driven into a facing position with a calibration assembly 400, as is shown in FIGS. 2 and 4. In addition, should the transducer array 28 accidentally bump into any portion of the reactor vessel during the inspection, it is desirable to verify transducer positioning to avoid, if possible, having to remove and decontaminate the inspection apparatus 14 in order to insure that there has been no disturbance of transducer mounting.

Figure 3:
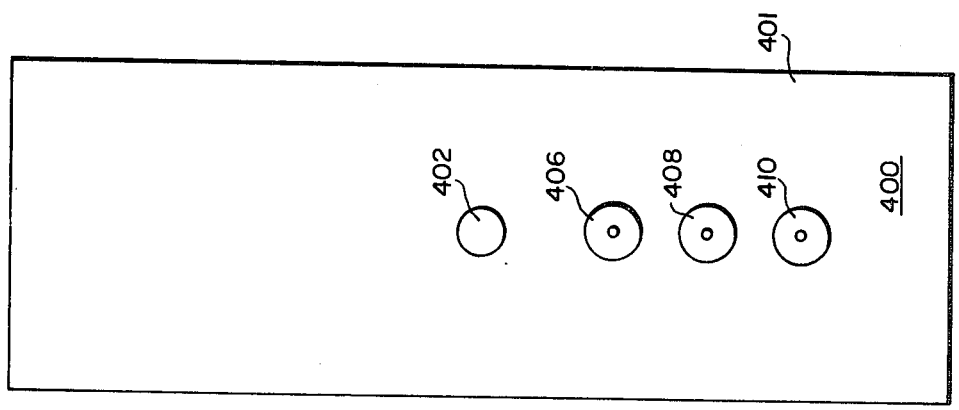
FIG. 3 is a top view of the calibration assembly shown in FIG. 3.

As shown in FIGS. 2 and 3, the calibration assembly 400 includes a generally rectangular plate 401 which, as shall be hereinafter explained, serves as an infinitely large reflecting surface for calibrating the perpendicularly mounted transducers in the array. A stand 404 is mounted at the approximate center of the plate 401 and carries thereon a small ball 402 which, as shall also be explained hereinafter, serves as an infinitely small reflecting surface for the perpendicularly mounted transducers. Also mounted on the same side of plate 401 are a plurality of upstanding truncated cones, in this embodiment three in number 406, 408 and 410, which are cut off at angles corresponding to expected angular settings of the transducers as mounted in the array 28. It will be appreciated by those having skill in this art that the shape of plate 401 and the location of stand 404 and of the cones 406, 408 and 410 is a matter of convenience. Further, to enhance the versatility of the calibration assembly 400, the cones 406, 408 and 410 can be fabricated from common stock or standards, such as stand 404, having an appropriately machined angular tip fastened thereto or an adjustable or removable tip which can be set to a desired angle as required. In any case, the various elements of the calibration assembly 400 will be fabricated from material which can readily withstand the hostile inspection environment.

The opposite side of plate 401 carries a clamp assembly 412 which engages the support leg 20A as is shown in FIGS. 2 and 4. A keyway 414 is cut into the clamp assembly 412 and engages a key 416 formed in the periphery of support leg 20A. The engagement of key 416 and keyway 414 insures that the calibration assembly 400 is properly oriented when mounted on support leg 20A. The calibration assembly 400 is tightly clamped to the support leg 20A by bolts 420 or some other suitable securing element.

FIG. 3 shows a top plan view of the ball 402 and the cones 406, 408 and 410. The distances therebetween are known as are the distances therefrom with respect to an arbitrary zero point on the plate 401. The tips of the cones 406, 408 and 410, in the preferred embodiment, are respectively cut at angles of 10°, 19° and 23°, but can be changed or adjusted to accommodate the particular angles at which certain of the transducers in array 28 are mounted.

In operation, the calibration assembly 400 is clamped to support leg 20A as is shown in FIGS. 1 and 3. Since the support leg 20A will sit in or on a known vessel location, the point at which the calibration assembly 400 is clamped to, is known in a rough sense. The carriage assembly 82 is then driven up or down the main column 24, along the Z axis, to a point where the transducer array plate 40 can be brought opposite the calibration assembly, as shown in FIG. 4. At that time, the operator will coarsely align one of the perpendicularly mounted transducers in array 28 with the ball 402. For convenience, only one transducer 244 has been shown in FIGS. 2 and 4.

With the transducer 244 in coarse alignment with the ball 402, it is actuated and thereupon emits an ultrasonic beam 403, as is best shown in FIG. 2. The beam reflection from the ball 402 will be the highest amplitude return signal and the operator continues to maneuver the transducer array 28 about by moving the appropriate segments of the manipulator arm 26 until satisfied that the reflection from ball 402 is the highest possible maximum signal received which means that the test transducer 244 and the ball 402 are in horizontal alignment. At this time, the reading of the Z axis or vertical resolver 102, which indicates the vertical position of the transducer array 28 or carriage assembly 82, is taken and is subsequently offset from future readings to calibrate or fix the future locations of the transducer array 28 with reference to the zero starting point just determined. At the same time, the perpendicularity of the mounting or alignment of transducer 244 can be verified as can be perpendicular alignment of all other transducers in array 28 which are so mounted.

Since the foregoing calibration test takes place with the inspection apparatus 14 in place in the reactor vessel, the calibration assembly 400 can also be used to verify or measure the speed of the transducer ultrasonic beam 403 in the operating medium, in this and other inspection cases, water. When the calibration transducer 244 is actuated, the resulting beam 403 has a slight spread as is shown in FIG. 2. The central portion 405 of the beam 403 strikes the ball 402, a relatively small surface, and is reflected therefrom back to transducer 244. The outer portion 407 of the beam 403 strikes plate 401, a relatively large surface for example at point 409 thereon, and is also reflected back to the transducer 244, but by a time delay which is a function of the distance between the ball 402 and the plate 401 and the medium in which the beam 403 travels. Since the height of the stand 404 is known, the water path distances from the transducer 244 to the ball 402 and from the transducer 244 to the plate 401 will also be known. Thus, the operator with the aid of an oscilloscope or other suitable device can calculate the time per unit of distance for the beam 403 in the operating medium. This calibration can be utilized later in the actual inspection to verify distances from the array 28 or any transducer therein to the vessel or any portion thereof.

In addition, after calibrating for and verifying the start position in the Z axis and the beam speed per unit of distance, the operator can verify the angular mounting of various other transducers in the array employing the angled reflecting surfaces of the cones 406, 408 and 410. To achieve this verification, the array 28 is driven to a point opposite the calibration assembly 400 in a manner similar to that shown in and described with respect to FIG. 4. In this instance, another of the transducers (not transducer 244) which has been angularly mounted in array 28 is brought into alignment with one of the cones 406, 408, or 410. That transducer is actuated and will receive a maximum reflected beam only if its angle of mounting corresponds with the angle formed in the tip of the cone at which it is directed. In this manner, the correctness of each of the mountings of the transducers in array 28 can be verified at any point in, before or after the inspection procedure. In the preferred embodiment, the tips of cones 406, 408 and 410 are truncated by machining them to a desired angle. Alternatively, the cones could be fabricated of identical stock or standards having angularly adjustable or removable tips.

While the invention has been shown and described herein in considerable detail, such dislosure is intended as being only illustrative or exemplary in character and not restrictive, as within the broad scope of the invention, modifications of or alternatives thereto may readily suggest themselves to persons skilled in the art.

I claim:

1. A calibration assembly for use in association with an ultrasonic transducer array of nuclear reactor vessel inspection apparatus, said assembly comprising:
   (a) a relatively large surface for reflecting an ultrasonic beam from any one of a predetermined number of transducers in the array, and
   (b) a relatively small surface for reflecting an ultrasonic beam from the same one of the transducers within the array, said small reflecting surface being positioned to be impinged by the ultrasonic beam prior to its impingement of the large reflecting surface at a predetermined distance therefrom.

2. The calibration assembly according to claim 1 which additionally comprises means for clamping said assembly to a predetermined portion of the inspection apparatus.

3. The calibration assembly according to claim 2 wherein said means for clamping includes means for automatically and properly orienting said calibration assembly on the predetermined portion of the inspection apparatus when clamping is effected.

4. The calibration assembly according to claim 3 which additionally comprises at least one additional reflecting surface, said additional reflecting surface being angled with respect to said large reflecting surface.

5. The calibration assembly according to claim 2 which additionally comprises at least one additional reflecting surface, said additional reflecting surface being angled with respect to said large reflecting surface.

6. The calibration assembly according to claim 1 which additionally comprises at least one additional reflecting surface, said additional reflecting surface being angled with respect to said large reflecting surface.

* * * * *